(12) United States Patent
Lancaster et al.

(10) Patent No.: US 8,507,572 B2
(45) Date of Patent: Aug. 13, 2013

(54) FUNCTIONALIZATION OF ORGANIC SURFACES

(75) Inventors: Jeffrey Lancaster, New York, NY (US); Nicholas J. Turro, Tenafly, NJ (US); Jeffrey T. Koberstein, Storrs, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 227 days.

(21) Appl. No.: 12/796,462

(22) Filed: Jun. 8, 2010

(65) Prior Publication Data

US 2010/0331441 A1    Dec. 30, 2010

Related U.S. Application Data

(60) Provisional application No. 61/185,061, filed on Jun. 8, 2009.

(51) Int. Cl.
*C08F 2/50*    (2006.01)
*C08F 2/42*    (2006.01)
*C08F 2/46*    (2006.01)

(52) U.S. Cl.
USPC ............... 522/39; 522/33; 522/34; 522/35; 522/46; 522/49; 522/50; 522/59; 522/63

(58) Field of Classification Search
USPC ............... 522/162, 166, 33, 34, 35, 39, 46, 522/49, 50, 59, 63
See application file for complete search history.

(56) References Cited

U.S. PATENT DOCUMENTS

| | | | |
|---|---|---|---|
| 2006/0165912 A1 | 7/2006 | Koberstein et al. | |
| 2008/0299046 A1 | 12/2008 | White et al. | |
| 2010/0099580 A1 | 4/2010 | Carroll et al. | |
| 2010/0331198 A1 | 12/2010 | Wang et al. | |
| 2012/0041546 A1* | 2/2012 | Belcheva et al. | 623/1.46 |
| 2012/0046737 A1* | 2/2012 | Belcheva et al. | 623/1.46 |
| 2012/0100633 A1* | 4/2012 | Manetto et al. | 436/501 |

FOREIGN PATENT DOCUMENTS

| | | |
|---|---|---|
| WO | WO-2005/060668 | 7/2005 |
| WO | WO-2010/053993 | 5/2010 |

OTHER PUBLICATIONS

Zhao et al. Synthesis and characterization of a polymerizable benzophenone derivative and its application in styrenic polymers as UV-stabilizer Original Research Article. European Polymer Journal, vol. 43, Issue 10, Oct. 2007, pp. 4541-4551.*

Tartaglino et al . Photobinding of [gamma-(32)P] ATP gamma-benzophenone to the surface of a polyurethane membrane in the preparation of a beta-particle-emitting balloon catheter. J Biomed Mater Res. 1999;48(5):669-74.*

(Continued)

*Primary Examiner* — Sanza McClendon
(74) *Attorney, Agent, or Firm* — Wilmer Cutler Pickering Hale and Dorr LLP

(57) ABSTRACT

The present invention relates to functionalizing a surface of an organic material. For example, surfaces of materials having C—H bonds, such as polymers having C—H bonds, can be functionalized. In certain embodiments, a heterobifunctional molecule having a photoactive anchor, a spacer, and a terminal functional group is applied to the surface of an organic material that contains one or more C—H bonds. The heterobifunctional molecule can be bound to any surface having C—H bonds as the photoactive anchor can react with C—H bonds upon irradiation. The terminal functional group has a "click" functionality which can be utilized to functionalize the surface of the organic material with any desired functionalizing moiety having the orthogonal click functionality.

18 Claims, 17 Drawing Sheets

(56) References Cited

OTHER PUBLICATIONS

Antoni et al., "Pushing the limits for Thiol-Ene and CuAAC Reactions: Synthesis of a 6th Generation Dendrimer in a single day," Macromolecules 2010, 43, 6625-6631.

Dondoni, "The Emergence of Thiol-Ene Coupling as a Click Process for MAterials and Bioorganic Chemistry," A. Angew. Chem. Int. Ed. 2008, 47, 8995-8997.

Fleming et al., "Triazole Cycloaddition as a General Route for Functionalization of AU Nanoparticles," *Chem. Mater.*, vol. 18, 2006, pp. 2327-2334.

Himo et al., "Copper(I)-Catalyzed synthesis of azoles. DFT study predicts unprecedented reactivity and intermediates,"*J. Am. Chem. Soc.*, vol. 127, 2005, pp. 210-216.

Huisgen, "Kinetics and Mechanism of 1,3-Dipolar Cycloadditions," *Angew. Chem. Int. Ed.*, vol. 2, No. 11, 1963, pp. 633-645.

Kolb et al, "Click Chemistry: Diverse Chemical Function from a Few Good Reactions," Angew. Chem. Int. Ed. 2001, 40, 2005-2021.

Lancaster et al., "Photopatterned "Click" Functional Polymer Surfaces," Polymer Preprints 2010, 51(1), 66-67.

Lewis et al., "Click Chemistry in Situ: Acetylcholinesterase as a reaction vessel for the selective assembly of a femtomolar inhibitor from an array of building blocks," *Angew. Chem. Int. Ed.*, vol. 41, No. 6, 2002, pp. 1053-1057.

Li et al., "Functionalization of Single-walled Carbon nanotubes with well-defined polystyrene by "click" coupling," *J. Am. Chem. Soc.*, vol. 127, 2005, pp. 14518-14524.

Moses, J. E. and Moorhouse, A. D., 'The Growing Applications of Click Chemistry, Chem. Soc. Rev 2007, 1249-1262.

Noodleman et al., "Quantum Chemical Studies of Intermediates and Reaction pathways in selected enzymes and catalytic synthetic systems," *Chem. Rev.*, vol. 104, 2004, pp. 459-508.

Punna et al., "Head-to-tail Peptide cyclodimerization by copper-catalyzed azide-alkyne cycloaddition," *Angew. Chem. Int. Ed.*, vol. 44, 2005, pp. 2215-2220.

Rodionov et al., Mechanism of the ligand-free $Cu^1$-catalyzed Azide-Alkyne Cycloaddition Reaction,' *Angew. Chem. Int. Ed.*, vol. 44, 2005, pp. 2210-2215.

Rostovtsev,V. V., Green, L. G., Fokin, V. V., Sharpless, K. B., "A Stepwise Huisgen cycloaddition process: Copper(I)-Catalyzed regioselective "Ligation" of Azides and terminal Alkynes," Angew. Chem. Int. Ed. 2002, 41, 2596-2599.

Sun et al., "Carbohydrate and Protein Immobilization onto Solid Surfaces by Sequential Diels-Alder and Azide-Alkyne Cycloadditions," Bioconjug Chem., vol. 17, pp. 52-57 (2006).

Tornoe, C. W., Christensen, C., Meldal, M., "Peptidotriazoles on Solid Phase: [1,2,3]—Triazoles by Regiospecific Copper(I)-Catalyzed 1,3- Dipolar Cycloadditions of Terminal Alkynes to Azides," J. Org. Chem. 2002, 67, 3057-3064.

* cited by examiner

R=H, TMS
n= 1-10

FUNCTIONALIZATION OF ORGANIC SURFACES

CROSS-REFERENCE TO RELATED APPLICATION

This application claims the benefit of the earlier filing date of U.S. Patent Application No. 61/185,061, filed on Jun. 8, 2009, the content of which is incorporated by reference herein in its entirety.

STATEMENT REGARDING FEDERALLY SPONSORED RESEARCH OR DEVELOPMENT

The invention was made with United States government support under Grant No. GK12 LEEFS 0742450 awarded by the National Science Foundation (NSF) through the Integrative Graduate Education and Research Traineeship (IGERT). The United States government has certain rights in this invention.

COPYRIGHT NOTICE

This patent disclosure may contain material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INCORPORATION BY REFERENCE

All patents, patent applications and publications cited herein are hereby incorporated by reference in their entirety. These disclosures in their entireties are hereby incorporated by reference into this application in order to more fully describe the state of the art as known to those skilled therein as of the date of the invention described herein.

FIELD OF THE INVENTION

The invention relates to functionalizing organic surfaces, such as polymers. More particularly, the invention relates to a method to attach molecules onto an organic surface, such as polymers or other surfaces that contains C—H bonds to provide the surface with functional groups capable of further reaction with any desired molecules.

BACKGROUND

The scientific literature on describing functionalization of hard substrates (e.g., glass, silicon, gold, etc.) is well-developed, and a number of different chemical anchors are known for hard surfaces. For example, silanes are known to be useful for attaching to glass and silicon surfaces and thiols are known to be useful for attaching to gold surfaces.

Comparable chemical anchors do not exist for organic surfaces (e.g., polymers or other surface that contain C—H bonds), partly because such surfaces have a wide variety of differing surface properties. As a result, a number of alternate techniques have been developed to functionalize organic surfaces by either specifically tailoring the technique to only a small number of particular chemistries or using techniques that are destructive in nature. For example, such techniques involve the incorporation of particular reactive groups into the polymer during the synthesis of the polymer, the synthesis of surface-specific block copolymers, or the degradation of the polymer via oxidation (ozonolysis) to provide functional groups on the surface.

SUMMARY

In accordance with the present invention, a heterobifunctional molecule that is capable of covalently binding to an organic surface by reacting with a C—H bond on the surface, a terminal functional group having a click functionality, and a spacer group that bridges the photoactive anchor and the terminal functional group is described. The terminal functional group is selected from the group consisting of alkyne, trimethylsilyl-protected alkyne, azide, nitrile, thiol, alkene, maleimide, streptavidin, biotin, antibody, antigen, integrin, fibronectin, epoxide, nucleophile, and thiiranium; and the photoactive anchor is selected from the group consisting of phthalimide, benzophenone, phenyl azide, xanthone, thioxanthone, sulfonyl azide, and phenyl diazirine.

In certain embodiments, the photoactive anchor is on a first end of the heterobifunctional molecule, the terminal functional group is at a second end of the heterobifunctional molecule and the terminal functional group consists of the click functionality, and the spacer group bridges the photoactive anchor at the first end and the terminal functional group at the second end.

In certain embodiments, the spacer is selected from the group consisting of oligomeric or polymeric forms of alkanes, alkane esters, alkane ethers, ethylene glycols, acetylenes, and phenylenes.

In certain embodiments, the photoactive anchor binds to the surface upon irradiation.

In certain embodiments, the photoactive anchor has a higher surface energy than the terminal functional group.

In certain embodiments, the photoactive anchor is a phthalimide and the terminal functional group is alkyne or a trimethylsilyl-protected alkyne.

In certain embodiments, the surface is the surface of a polymer.

In accordance with the present invention, a functionalized surface is described. The functionalized surface includes a material that comprises one or more C—H bonds on a surface of the material, the heterobifunctional molecule described above that is covalently bound to at least a portion of the surface of the material, where the heterobifunctional molecule has a click functionality, and a functionalizing moiety bound to the heterobifunctional molecule using an orthogonal click functionality.

In certain embodiments, the functionalizing moiety is a biomolecule, analyte, fluorophore, polymer, nanoparticle, anti-microbial material, phospholipid, dye, or chelator.

In certain embodiments, the functionalizing moiety is selected from the group consisting of DNAs, peptides, antibodies, and receptors.

In certain embodiments, the photoactive anchor is a phthalimide and the terminal functional group is alkyne or a trimethylsilyl-protected alkyne.

In accordance with the present invention, a method for functionalizing a surface is described. The method includes applying the heterobifunctional molecule described above to a surface of a material, irradiating the heterobifunctional molecule, and functionalizing the surface by reacting a functionalizing moiety with the heterobifunctional molecule using an orthogonal click functionality.

In certain embodiments, the method further includes applying a mask having a desired pattern prior to irradiating.

In certain embodiments, the photoactive anchor is on a first end of the heterobifunctional molecule, the terminal functional group is at a second end of the heterobifunctional molecule and the terminal functional group consists of the click functionality, and the spacer group bridges the photoactive anchor at the first end and the terminal functional group at the second end.

In certain embodiments, the spacer is selected from the group consisting of oligomeric or polymeric forms of alkanes, alkane esters, alkane ethers, ethylene glycols, acetylenes, and phenylenes.

In certain embodiments, the photoactive anchor binds to the surface upon irradiation.

In certain embodiments, the photoactive anchor has a higher surface tension than the terminal functional group.

In certain embodiments, the photoactive anchor is a phthalimide and the terminal functional group is alkyne or a trimethylsilyl-protected alkyne.

In certain embodiments, the material is a polymer.

In certain embodiments, the functionalizing moiety is a biomolecule, analyte, fluorophore, polymer, nanoparticle, anti-microbial material, phospholipid, dye, or chelator.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION

Heterobifunctional Molecules

Figure 1:
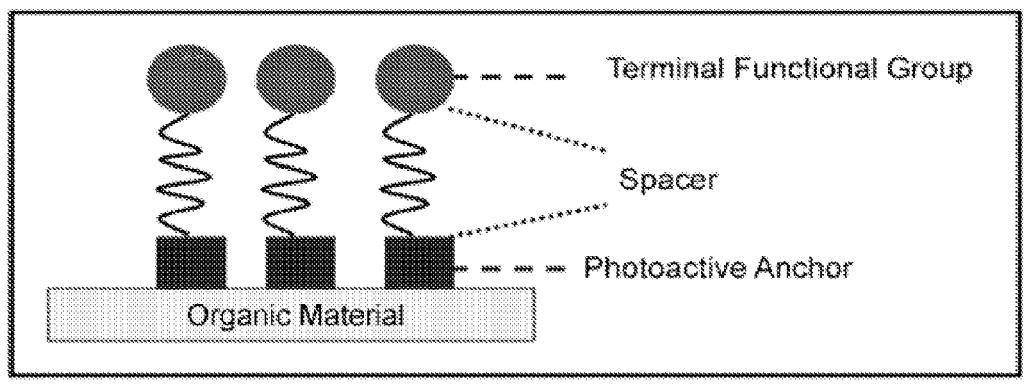
FIG. 1 is a schematic diagram of a heterobifunctional molecule that can be utilized to functionalize a surface of an organic material in accordance with certain embodiments.

The invention employs a heterobifunctional molecule that can be utilized to functionalize a surface of an organic material (e.g., polymers or other materials that contain C—H bonds). As shown in FIG. 1, the heterobifunctional molecule is comprised of a photoactive anchor that covalently binds to the surface of an organic material (such as a polymer or other materials that contain C—H bonds), a spacer, and a terminal functional group that can provide a "click" type chemistry or functionality.

Photoactive Anchor

As used herein, "photoactive anchor" is meant to encompass chemical groups or moieties that becomes reactive upon exposure to irradiation to bind to a surface of an organic material (e.g., polymers or other materials that contain C—H bonds).

In certain embodiments, the photoactive anchor that covalently binds to a surface of an organic material (e.g., materials that have C—H bonds) can have the following photoactive functionalities: phthalimide, benzophenone, phenyl azide, xanthone, thioxanthone, sulfonyl azides, phenyl diazirine, and other photoactive groups capable of covalent attachment, such as through hydrogen abstraction or carbene or nitrene insertion.

The photoactive anchor can be selected so that the photoactive anchor prefers to be near the surface of the organic material as compared to the terminal functional group. For example, the photoactive anchor may have a more favorable enthalpic interactions (e.g., lower surface tension) with the organic material relative to the terminal functional group.

The photoactive anchor can also be selected so that the excitation wavelength utilized to activate the photoactive group is selected to optimize favorable interactions with the surface of an organic material. In certain embodiments, the photoactive anchor can also be selected so that the excitation wavelength utilized to activate the photoactive group is selected to minimize unfavorable interactions with the surface of an organic material. For example, the photoactive anchor can be activated at excitation wavelengths which do not lead to crosslinking reactions of the surface of the organic material.

Spacers

As used herein, "spacer" is meant to encompass chemical groups or moieties that bridge the photoactive anchor and the terminal functional group.

In certain embodiments, the spacer can be comprised of alkanes, alkane esters, alkane ethers, and even oligomers and polymers, such as oligomeric and polymeric forms of ethylene glycol, polyacetylenes, polyphenylenes, and the like. In particular, conjugated spacers such as polyacetylenes and polyphenylenes can be used for electronics or light-harvesting applications. Generally, the spacer can have approximately 1-20 carbon atoms, such as $C_{1-20}$ alkanes, alkane esters, alkane ethers, or ethylene glycol having 1-20 repeat units. In certain embodiments, the spacer can have approximately 3-10 carbon atoms, such as $C_{3-10}$ alkanes, alkane esters, alkane ethers, or ethylene glycol having 3-10 repeat units.

In certain embodiments, the spacer can provide a suitable length to the heterobifunctional molecule so that the heterobifunctional can form a self-assembled monolayer when deposited on the surface of an organic material.

The spacer can be selected so that the presence of the spacer does not detrimentally affect exposure of the photoactive group to irradiation. In certain instances, the spacer can be transparent to the radiation wavelength utilized to activate the photoactive anchor so that the heterobifunctional molecule attaches to the surface of an organic material.

Terminal Functional Group

As used herein, "terminal functional group" is meant to encompass chemical groups or moieties that provide a desired functionality to the heterobifunctional molecule. Certain embodiments include chemical groups or moieties that provide a "click" functionality to the heterobifunctional molecule.

In certain embodiments, the terminal functional group can include alkyne, trimethylsilyl-protected alkyne, azide, nitrile, thiol, alkene, maleimide, streptavidin, biotin, antibody, antigen, integrin, fibronectin, epoxide, nucleophile, thiiranium, and the like.

As used herein, "click" functionality refers to reactions that have at least the following characteristics: (1) exhibits functional group orthogonality (i.e., the functional portion reacts only with a reactive site that is complementary to the functional portion, without reacting with other reactive sites); and (2) the resulting bond is irreversible (i.e., once the reactants have been reacted to form products, decomposition of the products into reactants is difficult). Optionally, "click" chemistry can further have one or more of the following characteristics: (1) stereospecificity; (2) reaction conditions that do not involve stringent purification, atmospheric control, and the like; (3) readily available starting materials and reagents; (4) ability to utilize benign or no solvent; (5) product isolation by crystallization or distillation; (6) physiological stability; (7) large thermodynamic driving force (e.g., 10-20 kcal/mol); (8) a single reaction product; (9) high (e.g., greater than 50%) chemical yield; and (10) substantially no byproducts or byproducts that are environmentally benign byproducts.

Examples of reactions using "click" functionalities can include, but are not limited to, addition reactions, cycloaddition reactions, nucleophilic substitutions, and the like. Examples of cycloaddition reactions can include Huisgen 1,3-dipolar cycloaddition, Cu(I) catalyzed azide-alkyne cycloaddition, and Diels-Alder reactions. Examples of addition reactions include addition reactions to carbon-carbon double bonds such as epoxidation and dihydroxylation. Nucleophilic substitution examples can include nucleophilic substitution to strained rings such as epoxy and aziridine compounds. Other examples can include formation of ureas and amides. Some additional description of click chemistry can be found in Huisgen, *Angew. Chem. Int. Ed.*, Vol. 2, No. 11, 1963, pp. 633-696; Lewis et al., *Angew. Chem. Int. Ed.*, Vol. 41, No. 6, 2002, pp. 1053-1057; Rodionov et al., *Angew. Chem. Int. Ed.*, Vol. 44, 2005, pp. 2210-2215; Punna et al., *Angew. Chem. Int. Ed.*, Vol. 44, 2005, pp. 2215-2220; Li et al., *J. Am. Chem. Soc.*, Vol. 127, 2005, pp. 14518-14524; Himo et al., *J. Am. Chem. Soc.*, Vol. 127, 2005, pp. 210-216; Noodleman et al., *Chem. Rev.*, Vol. 104, 2004, pp. 459-508; Sun et al., *Bioconjugate Chem.*, Vol. 17, 2006, pp. 52-57; and Fleming et al., *Chem. Mater.*, Vol. 18, 2006, pp. 2327-2334, the contents of which are hereby incorporated by reference herein in their entireties.

In certain embodiments, the heterobifunctional molecules can be designed so that the terminal functional group has a lower surface energy than the photoactive group so that the low surface energy will help orient the heterobifunctional molecules in the desired direction.

Particular Examples of Heterobifunctional Molecules

Figure 2A:
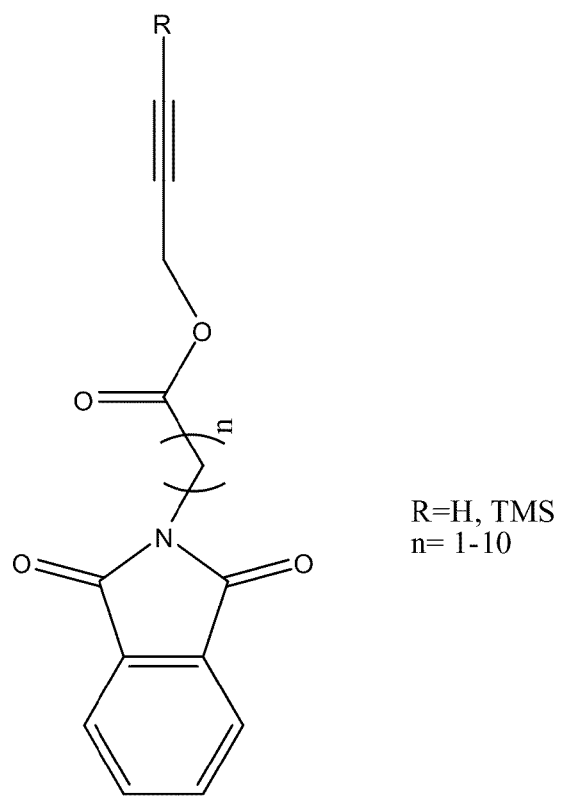
FIGS. 2A-2G are schematic diagrams of different exemplary heterobifunctional molecule that includes a various different photoactive groups, alkyl-ester spacer, and alkyne or trimethylsilyl-protected alkyne terminal functional group in accordance with certain embodiments.

In certain embodiments, as shown in FIG. 2A, the heterobifunctional molecule includes a phthalimide photoactive group having a spacer that includes alkanes and/or esters that is linked to a terminal alkyne or terminal trimethylsilyl-protected alkyne.

Figure 2B:
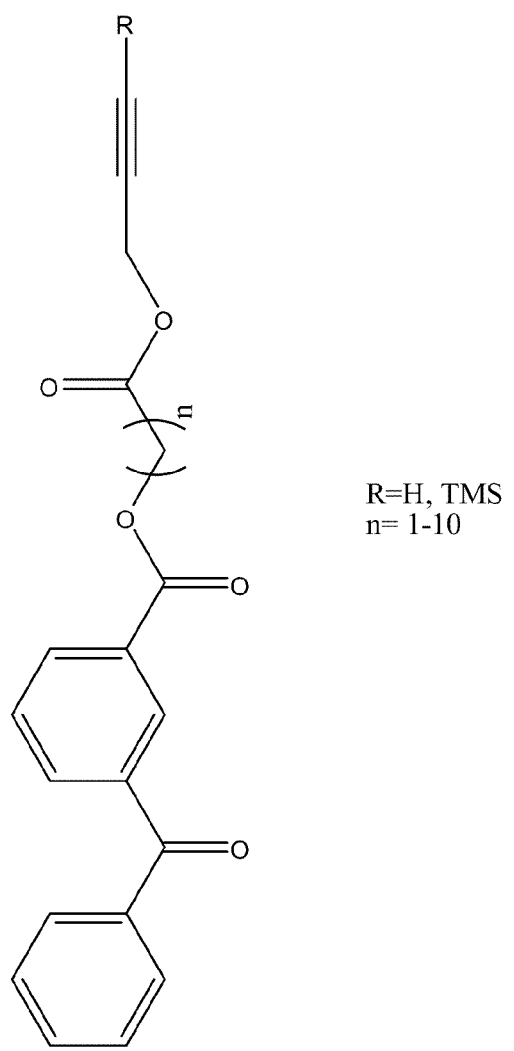

In certain embodiments, as shown in FIG. 2B, the heterobifunctional molecule includes a benzophenone photoactive group having a spacer that includes alkanes and/or esters that is linked to a terminal alkyne or terminal trimethylsilyl-protected alkyne.

Figure 2C:
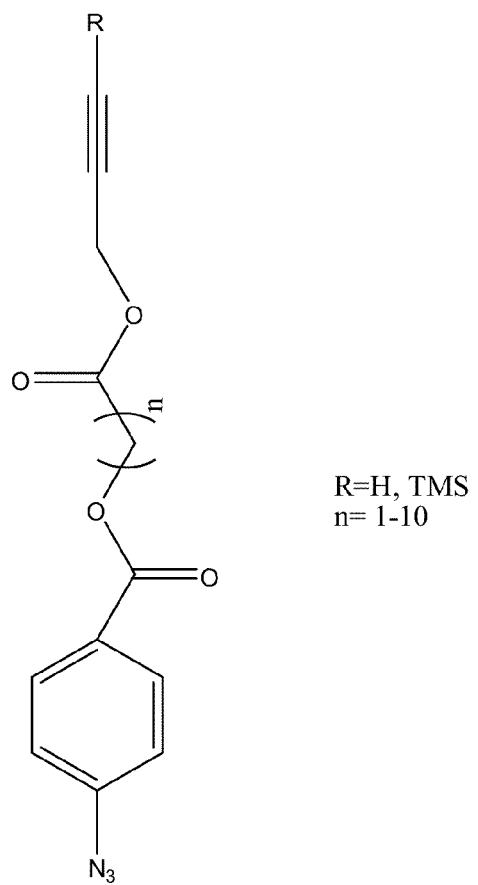

In certain embodiments, as shown in FIG. 2C, the heterobifunctional molecule includes a phenyl azide photoactive group having a spacer that includes alkanes and/or esters that is linked to a terminal alkyne or terminal trimethylsilyl-protected alkyne.

Figure 2D:
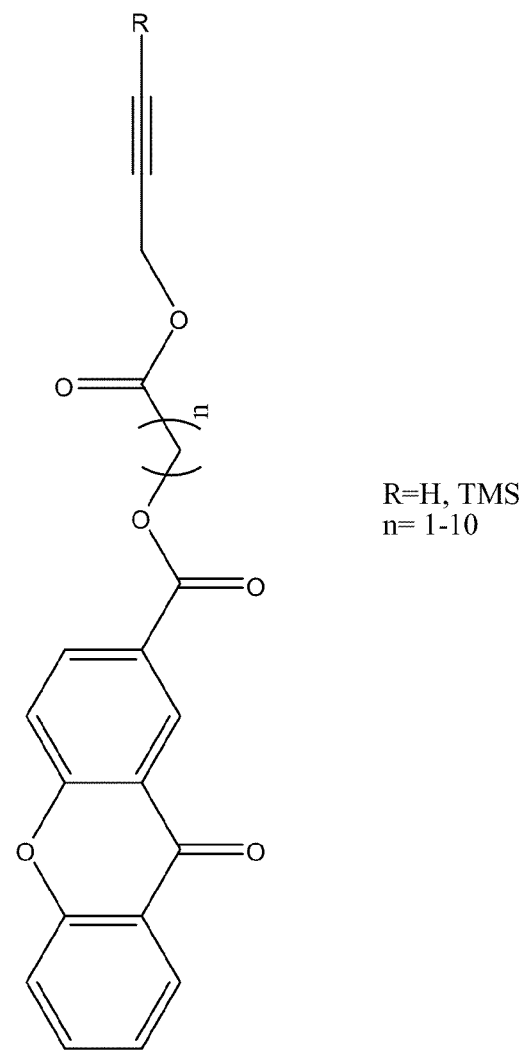

In certain embodiments, as shown in FIG. 2D, the heterobifunctional molecule includes a xanthone photoactive group having a spacer that includes alkanes and/or esters that is linked to a terminal alkyne or terminal trimethylsilyl-protected alkyne.

Figure 2E:
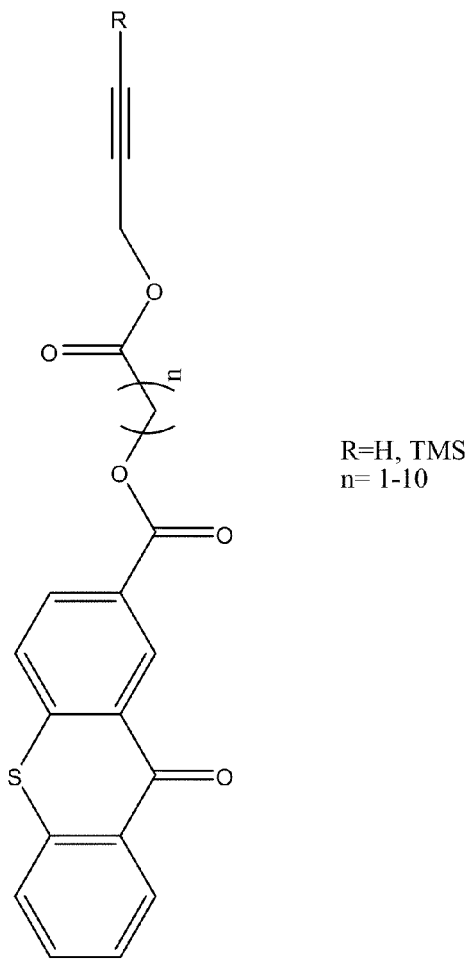

In certain embodiments, as shown in FIG. 2E, the heterobifunctional molecule includes a thioxanthone photoactive group having a spacer that includes alkanes and/or esters that is linked to a terminal alkyne or terminal trimethylsilyl-protected alkyne.

Figure 2F:
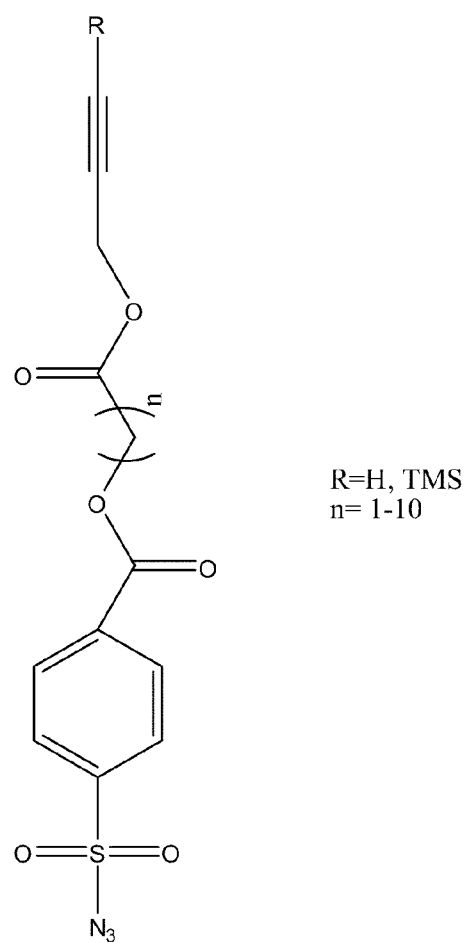

In certain embodiments, as shown in FIG. 2F, the heterobifunctional molecule includes a sulfonyl azide photoactive group having a spacer that includes alkanes and/or esters that is linked to a terminal alkyne or terminal trimethylsilyl-protected alkyne.

Figure 2G:
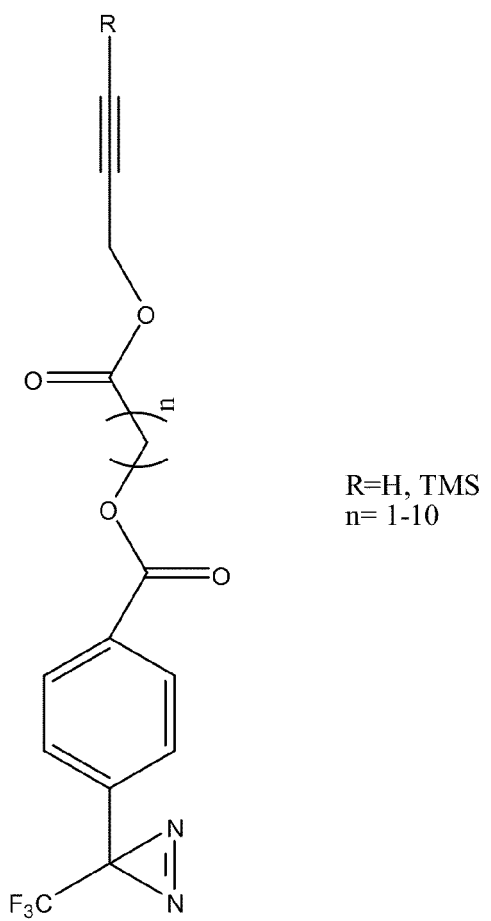

In certain embodiments, as shown in FIG. 2G, the heterobifunctional molecule includes a phenyl diazirine photoactive group having a spacer that includes alkanes and/or esters that is linked to a terminal alkyne or terminal trimethylsilyl-protected alkyne.

In certain embodiments, the exemplary heterobifunctional molecules can include a spacer that includes ether linkages in place of the ester linkages shown.

Synthesis of the Heterobifunctional Molecule

Heterobifunctional molecule of the present invention can be synthesized in a number of different methodologies.

In certain embodiments, a molecule having the terminal functional group attached to a spacer can be formed. Subsequently, the photoactive anchor can be attached thereon to obtain the heterobifunctional molecule.

Alternatively, a molecule having the photoactive anchor attached to a spacer can be formed. Subsequently, the terminal functional group can be attached thereon to obtain the heterobifunctional molecule.

First Reaction Step

In certain embodiments, a molecule having a terminal functional group attached to a spacer can be formed.

Figure 3:
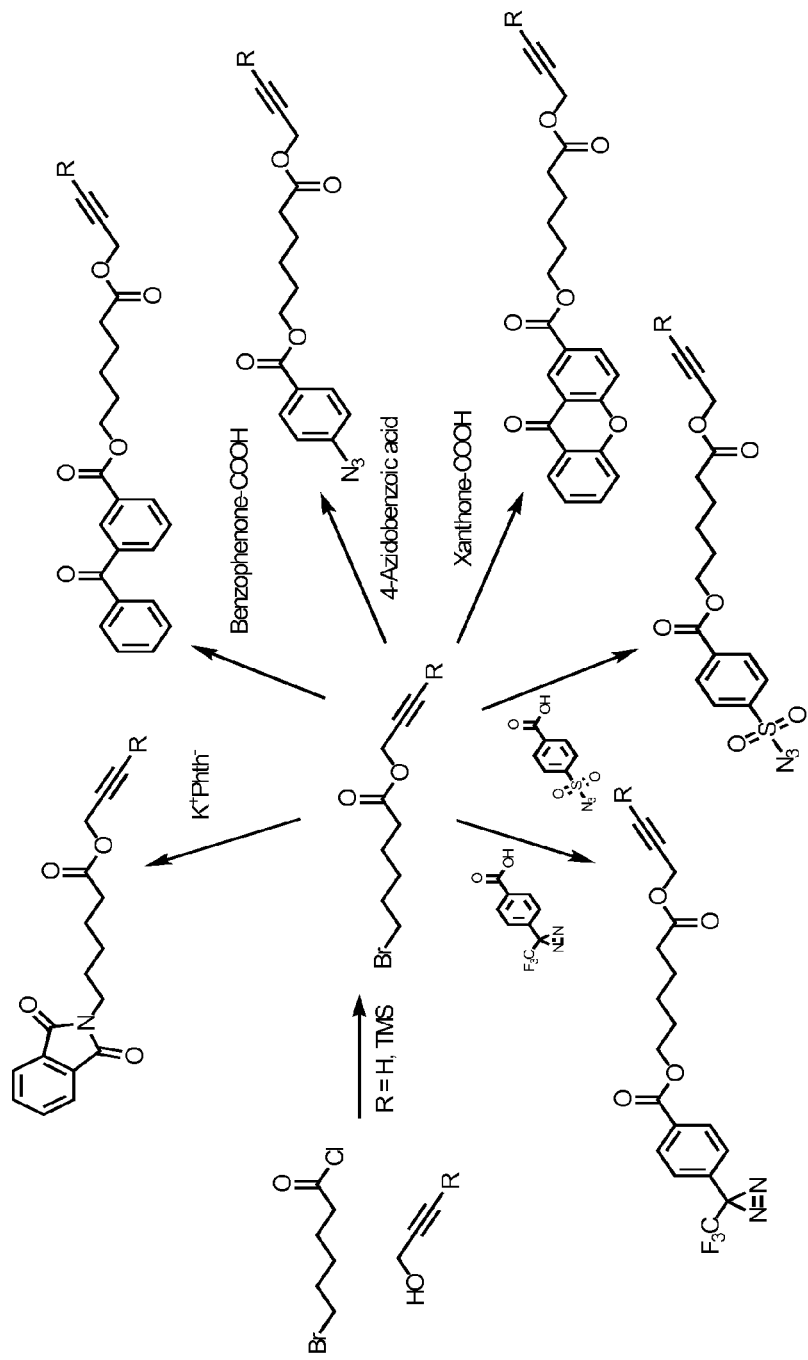
FIG. 3 is a schematic diagram illustrating the different exemplary synthetic techniques that can be employed to obtain the different exemplary heterobifunctional molecules in accordance with certain embodiment.

For example, as shown in FIG. 3, in a first reaction step, condensation reaction can be carried out using n-bromoalkanoyl chloride and a suitable alcohol, such as propargyl alcohol or 3-trimethylsilyl-propargyl-1-ol to obtain the alkyne or trimethylsilyl-protected alkyne terminal functional groups having a desired spacer, where n can range from, for example, 1 to 20.

In such example, the alkyne or trimethylsilyl-protected alkyne terminal functional group can be utilized for subsequent copper catalyzed 1,3-dipolar cycloaddition (CuAAC) with a desired molecule having an azide moiety. The particular benefits of the alkyne or trimethylsilyl-protected alkyne terminal functional group are (a) its low surface energy to aid in the orientation of the heterobifunctional molecule on the polymer surface, (b) the ease of optional protection by the trimethylsilyl group, and (c) the ease of deprotection of the trimethylsilyl protecting group through a benign chemistry.

Other desired terminal functional groups can be easily synthesized if the desired "click" chemistry is different. For example, if the desired "click" chemistry is a thiol-ene reaction, the terminal functional group can be modified to carry either a thiol or an alkene group. If the desired "click" chemistry is a nitrile-azide reaction, the terminal functional group can be modified to carry a nitrile group. Other suitable modifications are possible.

In yet another example, carbodiimide coupling of a n-bromo-1-ol to any a number of commercially available maleimide-carboxylic acids (e.g. 4-maleimidobutyric acid, 6-maleimidohexanoic acid) can yield a maleimide-functional molecule for subsequent photofunctionalization in the second reaction step. This class of molecule may be appropriate for Diels-Alder coupling to a diene-functionalized analyte.

Second Reaction Step

Subsequently, the molecule having a terminal functional group attached to a spacer can be reacted to attach the photoactive group to obtain the heterobifunctional molecule. Some exemplary synthetic schematic is shown in FIG. 3, as more fully described below.

For example, a phthalimide photoactive anchor can be obtained by the reaction of the molecule obtained in the first reaction step described above with a potassium phthalimide salt to produce the heterobifunctional molecule.

In another example, a benzophenone photoactive anchor can be obtained by the reaction of the molecule obtained in the first reaction step described above with a 3-(or 4)-benzoylbenzoic acid in a strong base environment to produce the heterobifunctional molecule.

In another example, a phenyl azide photoactive anchor can be obtained by the reaction of the molecule obtained in the first reaction step described above with 4-azidobenzoic acid in a strong base environment to produce the heterobifunctional molecule.

In another example, a xanthone photoactive anchor can be obtained by the reaction of the molecule obtained in the first reaction step described above with carboxylic acid derivative of xanthone in a strong base environment to produce the heterobifunctional molecule.

In another example, a sulfonyl azide photoactive anchor can be obtained by the reaction of the molecule obtained in the first reaction step described above with 4-sulfonylazide-benzoic acid in a strong base environment to produce the heterobifunctional molecule.

In another example, a diazirine photoactive anchor can be obtained by the reaction of the molecule obtained in the first reaction step described above with 4-(trifluoromethyldiazirine)benzoic acid in a strong base environment to produce the heterobifunctional molecule.

Alternatively, reaction of the molecule obtained in the first reaction step described above with the hydroxyl derivatives of the photoactive moieties in acetone with potassium carbonate can generate comparable molecules with ether linkages in place of the ester linkages shown in FIGS. 2A through 2G.

Functionalizing Polymer Surfaces

The heterobifunctional molecules described above can be utilized to functionalize any materials that is reactive with the photoactive group. For example, any surface of a material that contains C—H bonds, such as a polymer surface having C—H bonds, can be functionalized to have any desired coating thereon.

Figure 4:
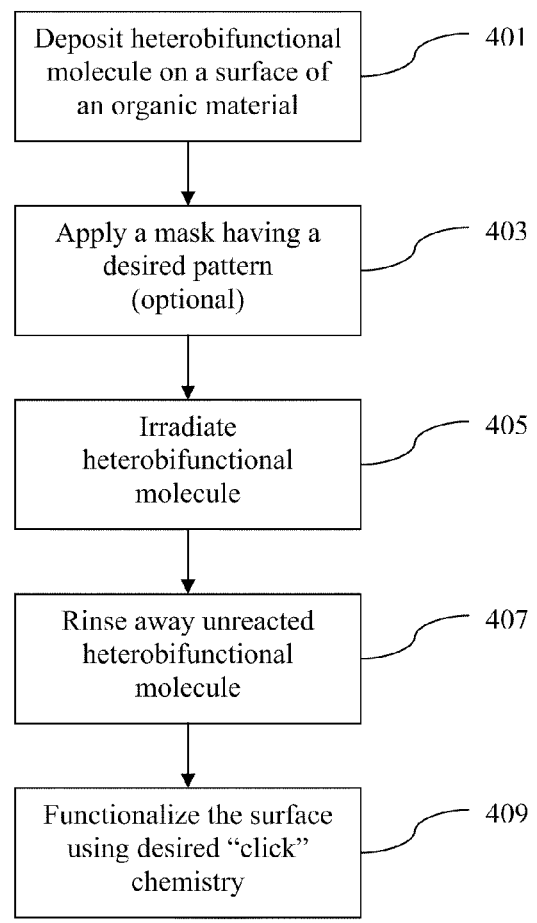
FIG. 4 is a flow chart to describe a method to functionalize a surface of an organic material in accordance with certain embodiments.

To functionalize a surface of an organic material, as shown in 401 of FIG. 4, the heterobifunctional molecule can be applied to a surface of an organic material in any suitable manner. For example, the heterobifunctional molecule can be applied to a surface using a 1% (w/w) solution in an appropriate solvent (e.g., organic liquids such as ethanol, methanol, propanol, toluene, diglyme, acetone, and the like or inorganic liquids such as water, or combinations thereof) by spin-coating, drop-casting, dip-casting, spray casting, evaporation, vapor deposition, and the like.

In certain embodiments, the heterobifunctional molecule can be utilized to photo-pattern (e.g., using irradiation to create a pattern) "click" type chemistry or functionality on a polymer surface. For example, as shown in 403 of FIG. 4, a mask having a desired pattern can optionally be utilized to selectively anchor the heterobifunctional molecules to desired areas of the surface of an organic material.

As shown in 405 of FIG. 4, the heterobifunctional molecules can be covalently bound to a surface of an organic material by activating the photoactive anchor (e.g., phthalimide, benzophenone, phenyl azide, etc.) with irradiation, such as visible light, ultraviolet light, and the like. For example, irradiation using a 300 nm lamp can bind a phthalimide heterobifunctional molecule to the surface.

In certain embodiments, irradiation through a mask can result in a 'positively' patterned surface where the heterobifunctional molecules bind to the surface wherever the heterobifunctional molecule is exposed to the irradiation.

In some other embodiments, the surface may also be 'negatively' patterned after a first functionalization step over the entire surface followed by irradiation through a mask in the presence of a photoacid generator. In this case the ester linkage can be cleaved by the acid which has been produced from the reaction of the light and the photoacid generator, effecting the release of the alkyne functionality as a free small molecule. In the negative pattern, only the functional alkyne molecules can remain that are not impinged by light through the mask. Such negative functionalization technique may be useful when multiple "click" functionalities in diverse patterns are desired on the surface.

Then, as shown in 407 of FIG. 4, any unreacted molecule that did not covalently bind to the surface of an organic material can be rinsed away using suitable liquids or gases, such as ethanol, water, toluene, supercritical $CO_2$, and the like. Selection of appropriate solvents can depend on the properties of the surface to be functionalized.

Then, as shown in 409 of FIG. 4, the anchored heterobifunctional molecule surface can then be utilized for subsequent 'click' chemistry using any molecule having an orthogonal "click" functionality. For example, when a heterobifunctional molecule having a alkyne or trimethylsilyl-protected alkyne terminal functional group is used, subsequent 'click' reaction with a desired molecule having azide group can be utilized to functionalize the polymer surface, using, for example, as copper-catalyzed azide-alkyne cycloaddition (CuAAC).

Depending on the nature of the molecule 'clicked' onto the alkyne-functionalized polymer surface, a number of functionalized surfaces can be produced, including but not limited to biomolecule-functionalized surfaces for biological assays, analyte-functionalized surfaces for sensors, fluorophore-functionalized surfaces, anti-microbial-functionalized surfaces, and secondarily functionalized surfaces to selectively bind other molecules.

Advantages

The present invention provides the long-sought-after ability to functionalize almost any type of a surface that contains C—H bonds by application of a universal linker molecule. In particular, the present invention allows functionalizing any polymers or other organic materials that contain C—H bonds by attaching the heterobifunctional molecule to provide a "click" functionality on the surface, which can then be utilized to attach any desired molecule having the orthogonal "click" functionality. The invention provides a facile and reliable method to pattern almost any surface that has C—H bonds and can be characterized as a universal surface patterning technique for surfaces of organic materials that contains C—H bonds.

Whereas the conventional techniques were focused mostly on methods to functionalize only hard substrates, the present invention provides methods to achieve a wide variety of different desired functionalities on even soft substrates using the heterobifunctional molecule described above and a desired molecule having the orthogonal "click" functionality. Because the "click" functional group is available for subsequent secondary functionalization, functionalities not previously available are now possible to achieve.

A molecule that allows attachment to almost any type of a surface that contains C—H bonds and thereafter providing the capability to attach any desired molecules is both superior and unexpected. In fact, because such organic materials were thought to exhibit vastly differing chemical properties, it was long thought that specific chemistries had to be developed for each surface intended to be functionalized. For example, earlier work involved synthesis of block copolymers, where one block was the same or similar to the surface of the material to be functionalized and the other block had the desired functionalizing chemical moieties. Accordingly, for a new material that had to be functionalized, a new block copolymer had to be synthesized.

In contrast, the present invention provides a heterobifunctional molecule that provides the ability to provide any surface having C—H bonds with a "click" functionality. The "click" functionality can then be utilized to attach any desired molecule thereon.

Furthermore, because the invention involves the irradiation of the surface to attach the heterobifunctional molecule, the natural benefit to this approach is the ease of patternability for the surface. That the process is easily patterned increases its potential for uses in electronics, assays, and nanoarchitectural applications.

Example

The following materials and instrumentation were used in the Example set forth below.

All reagents were used without further purification. 6-bromohexanoyl chloride, propargyl alcohol, 3-(trimethylsilyl) propargyl alcohol, phthalimide potassium salt, sodium azide, and poly(acrylic acid) (35 wt % solution in water, avg. $M_w$=100,000) were purchased from Sigma Aldrich. Polystyrene ($M_p$=1,056,000, $M_w/M_n$=1.03) was purchased from Polymer Laboratories.

$^1$H NMR spectra were obtained using a Bruker 400 MHz spectrometer. ATR-IR spectra were obtained using a Nicolet Nexus 870 FT-IR with an Avatar Smart Multi-bounce HATR accessory. Water contact angles were obtained using deionized water (>18.2 MΩ cm, Millipore, Milli-Q) and measured at room temperature using a 100-0° contact angle goniometer (Rame-Hart, Inc.). FTIR spectra were obtained using a home-built apparatus in transmission mode with a DTGS detector.

Prop-2-ynyl 6-(phthalimido)hexanoate (Phth-≡-H) and 3-(trimethylsilyl)prop-2-ynyl 6-(phthalimido)hexanoate (Phth-≡-TMS) were synthesized as shown below.

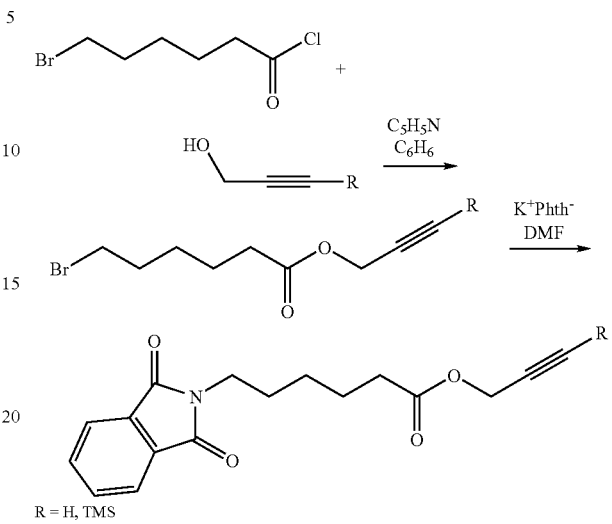

R = H, TMS

As shown, the syntheses involved the condensation of an acid chloride with a terminal or 1-trimethylsilyl-protected 1-alkyn-3-ol followed by displacement of bromine by phthalimide. The detailed synthetic techniques are more fully described below.

Synthesis of Prop-2-ynyl 6-(phthalimido)hexanoate (Phth-≡-H)

Synthesis of Prop-2-ynyl 6-bromohexanoate

Propargyl alcohol (0.5 mL, 3.41 mmol, 1 eq.) was dissolved in 10 mL of dry pyridine and 10 mL of dry benzene under argon and this solution was cooled in an ice bath. 6-bromohexanoyl chloride (0.612 mL, 4.1 mmol, 1.2 eq.) dissolved in 10 mL of dry benzene under argon was then added dropwise to the propargyl alcohol solution and stirred overnight. The solution was acidified with 1M HCl, then extracted twice with $CH_2Cl_2$. The organic layers were twice washed with 1M NaOH, once washed with brine, and dried over $Na_2SO_4$. The solvent was removed on a rotary evaporator to yield a light brown oil.

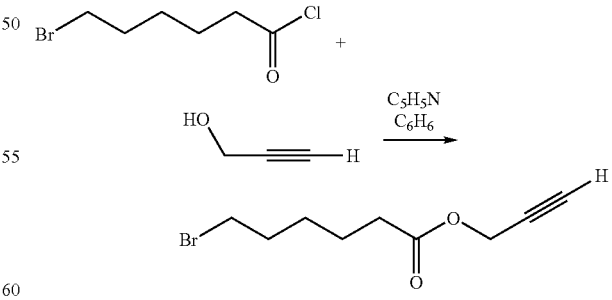

Synthesis of Prop-2-ynyl 6-(phthalimido)hexanoate (Phth-≡-H)

Prop-2-ynyl 6-bromohexanoate (0.606 g, 2 mmol, 1 eq.) was added to a solution of phthalimide potassium salt (0.441 g, 2.4 mmol, 1.2 eq.) in 50 mL of DMF and stirred overnight under argon. CHCl₃ was added to the solution flask and was transferred to a separatory funnel containing water. The aqueous layer was separated and twice extracted with CHCl₃. The combined organic layers were twice extracted with water then the solvent was removed on a rotary evaporator. Remaining solvent was removed under high vacuum overnight to yield a brown oil.

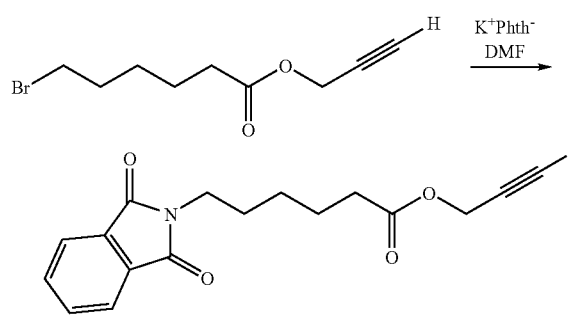

Synthesis of 3-(trimethylsilyl)prop-2-ynyl 6-(phthalimido)hexanoate (Phth-≡-TMS)

Synthesis of 3-(trimethylsilyl)prop-2-ynyl 6-bromohexanoate 3-(trimethylsilyl)proparyl alcohol (0.5 mL, 3.41 mmol, 1 eq.) was dissolved in 10 mL of dry pyridine and 10 mL of dry benzene under argon and this solution was cooled in an ice bath. 6-bromohexanoyl chloride (0.612 mL, 4.10 mmol, 1.2 eq.) dissolved in 10 mL of dry benzene under argon was then added dropwise to the 3-(trimethylsilyl)proparyl alcohol solution and stirred overnight. The solution was acidified with 1M HCl, then extracted twice with CH₂Cl₂. The organic layers were twice washed with 1M NaOH, once washed with brine, and dried over Na₂SO₄. The solvent was removed on a rotary evaporator to yield a light brown oil.

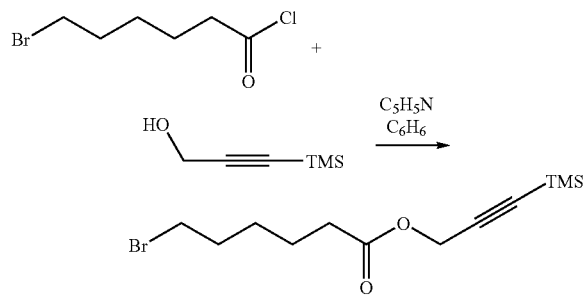

Synthesis of 3-(trimethylsilyl)prop-2-ynyl 6-(phthalimido)hexanoate (Phth-≡-TMS)

3-(trimethylsilyl)prop-2-ynyl 6-bromohexanoate (0.606 g, 2 mmol, 1 eq.) was added to a solution of phthalimide potassium salt (0.4412 g, 2.4 mmol, 1.2 eq.) in 50 mL of DMF and stirred overnight under argon. CHCl₃ was added to the solution flask and was transferred to a separatory funnel containing water. The aqueous layer was separated and twice extracted with CHCl₃. The combined organic layers were twice extracted with water then the solvent was removed on a rotary evaporator. Remaining solvent was removed under high vacuum overnight to yield a brown oil.

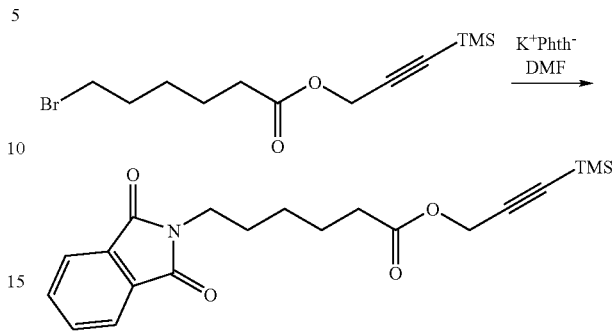

Characterization of Phth-≡-H and Phth-≡-TMS

Figure 5:
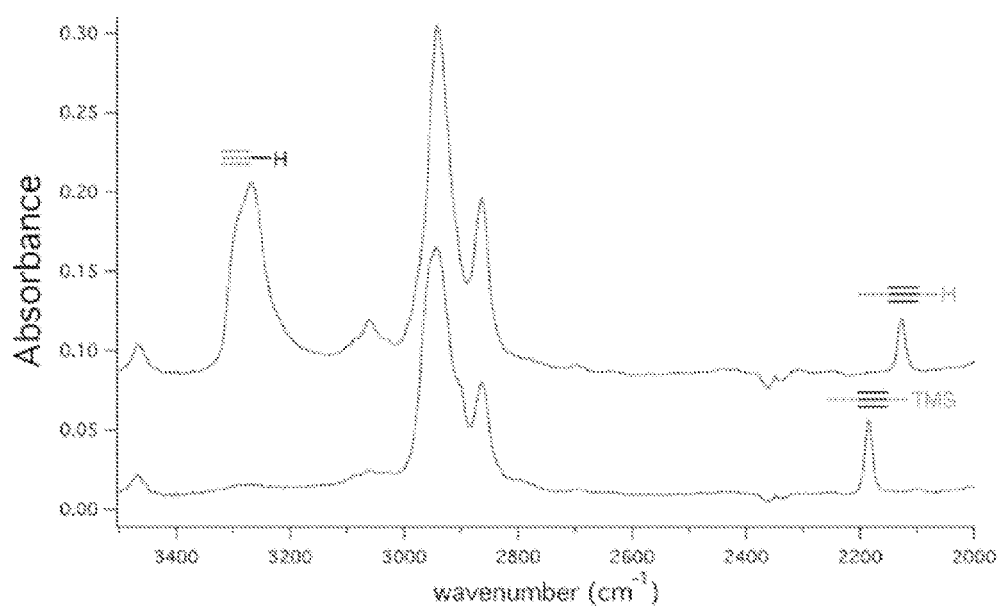
FIG. 5 shows a Fourier transform infrared spectra for prop-2-ynyl 6-(phthalimido)hexanoate and 3-(trimethylsilyl)prop-2-ynyl 6-(phthalimido)hexanote in accordance with certain embodiments.

FIG. 5 shows the assigned infrared (IR) spectra for Prop-2-ynyl 6-(phthalimido)hexanoate (Phth-≡-H) and 3-(trimethylsilyl)prop-2-ynyl 6-(phthalimido)hexanoate (Phth-≡-TMS). The IR spectra are effectively identical in the region from 2000-3500 cm⁻¹ except for the stretches resulting from the different alkyne functionalities. The terminal alkyne exhibits both a C—H stretch at 3250 cm⁻¹ and a C≡C stretch at 2120 cm⁻¹ while the TMS-protected alkyne exhibits a C≡C stretch at the slightly higher frequency of 2190 cm⁻¹ and no terminal C—H stretch, as is expected.

Figure 6:
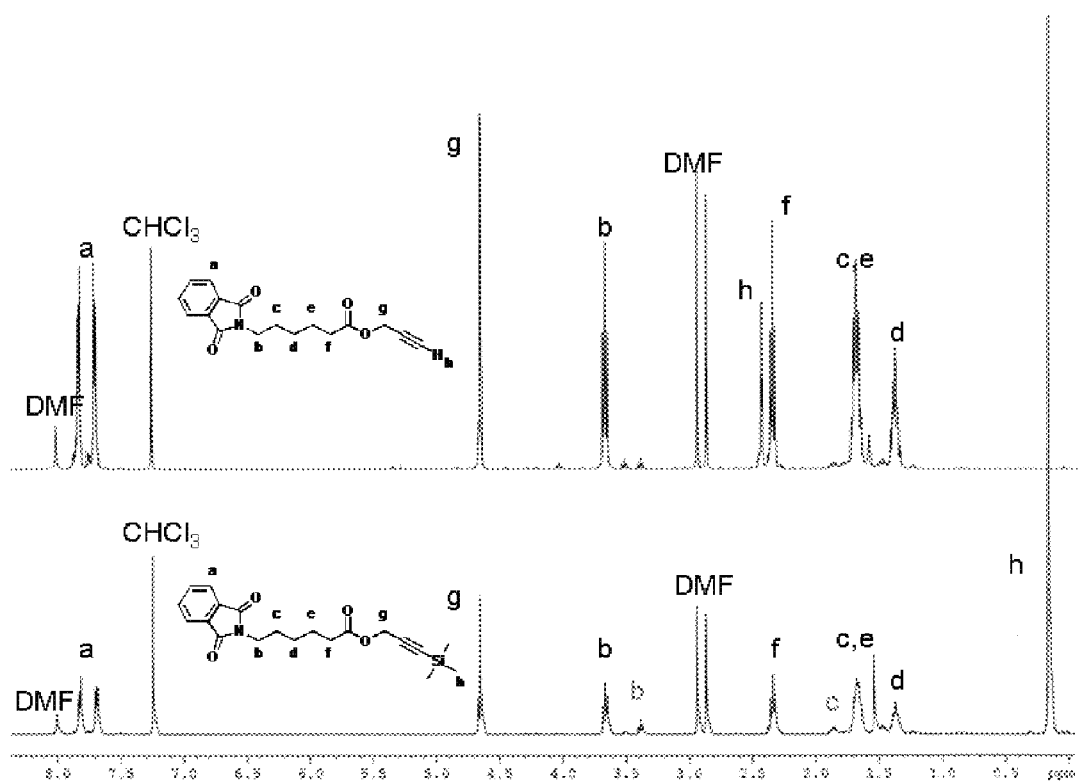
FIG. 6 shows a $^1$H NMR spectra for prop-2-ynyl 6-(phthalimido)hexanoate and 3-(trimethylsilyl)prop-2-ynyl 6-(phthalimido)hexanote in accordance with certain embodiments.

Additionally, FIG. 6 shows the ¹H NMR spectra for the two compounds. As shown, the spectra are identical except for the terminal alkynyl proton (1H) which is shifted to δ2.4 ppm whereas the trimethylsilyl protons (9H's) are shifted to δ0.15 ppm.

Mass spectra (FAB+) (not shown) showed the appropriate M+1 molecular weight peaks at 300.45 for the terminal alkyne derivative and 372.2 for the TMS-alkyne derivative.

Functionalization of Polymer Surfaces

Figure 7:
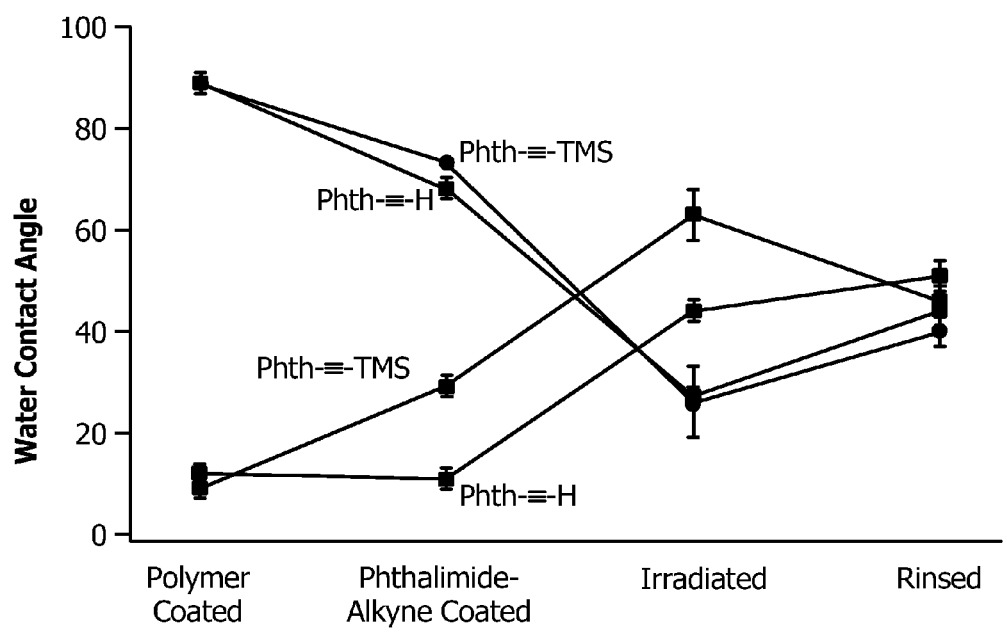
FIG. 7 shows the various contact angle measurements as the heterobifunctional molecules are applied and covalently bound to a polymer surface in accordance with certain embodiments.

Two different polymer surfaces were utilized. The polymers—polystyrene (PS) and poly(acrylic acid) (PAA) were selected as model polymers because of their differing hydrophobicity and hydrophilicity, as evidenced by the contact angles. As shown in FIG. 7, the initial contact angle for polystyrene was approximately 90° (i.e., hydrophobic) and the initial contact angle for poly(acrylic acid) was approximately 10° (i.e., hydrophilic).

The PS and PAA polymer surfaces were then each coated with Phth-≡-H and Phth-≡-TMS. The contact angles were measured again as shown in FIG. 7. As shown, PAA coated with Phth-≡-H had little change in contact angle. PAA coated with Phth-≡-TMS increased its contact angle to about 30°. PS coated with Phth-≡-H and Phth-≡-TMS decreased its contact angles to about 70°.

FTIR spectroscopy was also utilized to verify that the PS polymer surface were coated with Phth-≡-H. A peak at 3260 cm⁻¹ is assigned to a terminal alkyne C—H stretch and can act as an indicator of the presence of Phth-≡-H on the PS surface.

Figure 8:
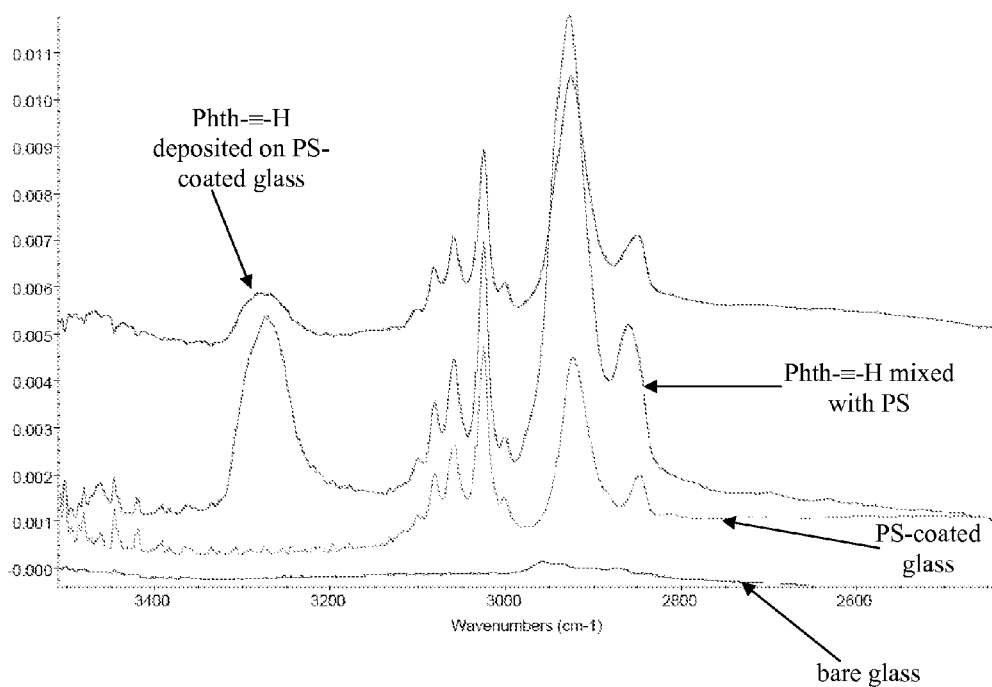
FIG. 8 shows a Fourier transform infrared spectra for glass slide, polymer, and a heterobifunctional molecule deposited on or mixed with the polystyrene (PS) in accordance with certain embodiments.

FIG. 8 shows the FTIR spectra of a bare glass slide (bottom curve) and the glass slide with a PS film coated thereon (second to bottom curve). In both of these spectra, no peak is present at 3260 cm⁻¹. Upon coating the PS film with Phth-≡-H, a peak begins to appear at 3260 cm⁻¹ indicating the presence of the Phth-≡-H as shown at the top curve of FIG. 8. As further verification, Phth-≡-H was physically mixed with PS and the film was cast, showing a dramatic increase in the signal at 3260 cm$^{-1}$, which is expected as more Phth-≡-H is incorporated into the sample.

The Phth-≡-H and Phth-≡-TMS coated PS and PAA polymers were then irradiated. The amount of irradiation can range anywhere from a few seconds to a few hours. For initial experiments, irradiation was carried out for two hours to ensure reaction of the phthalimide anchor with the underlying PS and PAA polymer surfaces. The contact angles were measured again as shown in FIG. 7. As shown, PAA coated with Phth-≡-H increased its contact angle to about 40°. PAA coated with Phth-≡-TMS increased its contact angle to about 60°. PS coated with Phth-≡-H and Phth-≡-TMS decreased the contact angle to about 30°. Without wishing to be bound by theory, the drastic change in the contact angle observed following irradiation may be indicative of small molecule reordering as a result of H-abstraction-induced covalent bonding of the phthalimide to the polymer surfaces.

After irradiation, the surfaces were rinsed with ethanol and water and the contact angles were measured again. As shown in FIG. 7, all the samples exhibit contact angles in the range of about 40° to 50°. It should be noted that TMS-protection of the alkyne does not have a significant effect on the final surface energy as evidenced by the comparable water contact angles. Without wishing to be bound by theory, the fact that the water contact angles for both the phthalimide-alkyne and the TMS-protected phthalimide-alkyne approach the same range of surface energies after irradiation and rinsing, this may indicate that the water drop interacts with a similar alkyne surface despite the underlying hydrophobic PS or hydrophilic PAA films.

It should also be noted that these preliminary experiments indicated two hours of irradiation may be ablating the PS film. As a result, the irradiation time was varied from 0 to 30 minutes to optimize attachment of the Phth-≡-H and Phth-≡-TMS without ablating the underlying polymer substrate.

Figure 9:
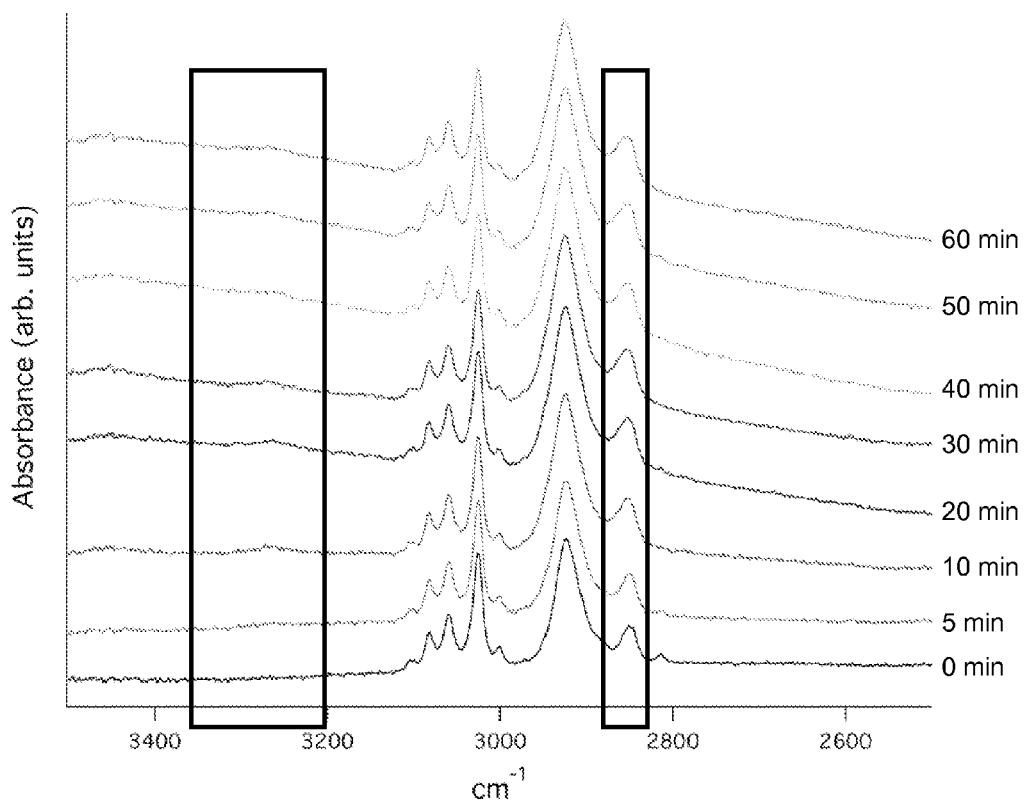
FIG. 9 shows a Fourier transform infrared spectra for prop-2-ynyl 6-(phthalimido)hexanoate bound on PS as a function of different irradiation times in accordance with certain embodiments.
Figure 10:
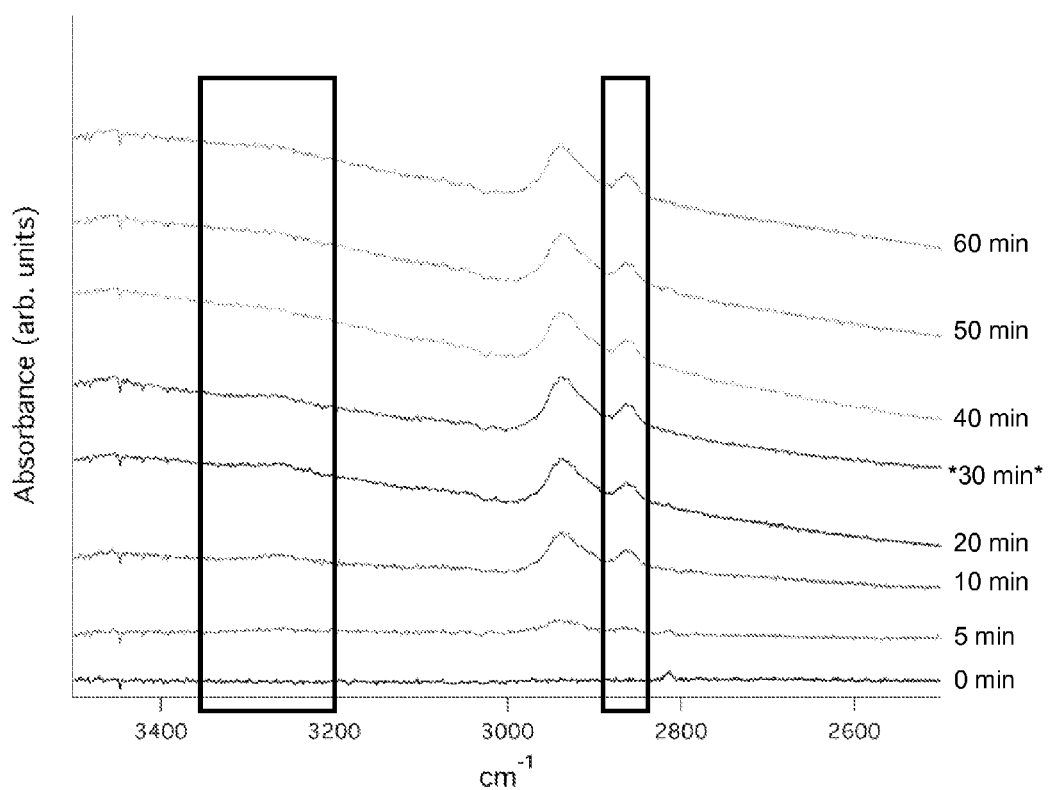
FIG. 10 shows a Fourier transform infrared spectra for prop-2-ynyl 6-(phthalimido)hexanoate bound on PS after the PS signal has been subtracted out as a function of different irradiation times in accordance with certain embodiments.

FIG. 9 shows the FTIR of Phth-≡-H as a function of different irradiation times. FIG. 10 shows the FTIR signal after the FTIR signals from the PS has been subtracted out. As shown in FIG. 10, without irradiation and after rinsing, (see curve for "0 min" in FIG. 10), no peak corresponding to Phth-≡-H was observed. The peaks corresponding to Phth-≡-H appeared with irradiation (see peaks in the highlighted black boxes at 2850 cm$^{-1}$) and increased with longer irradiation times until the intensity leveled off at about 30 minutes of irradiation.

Figure 11:
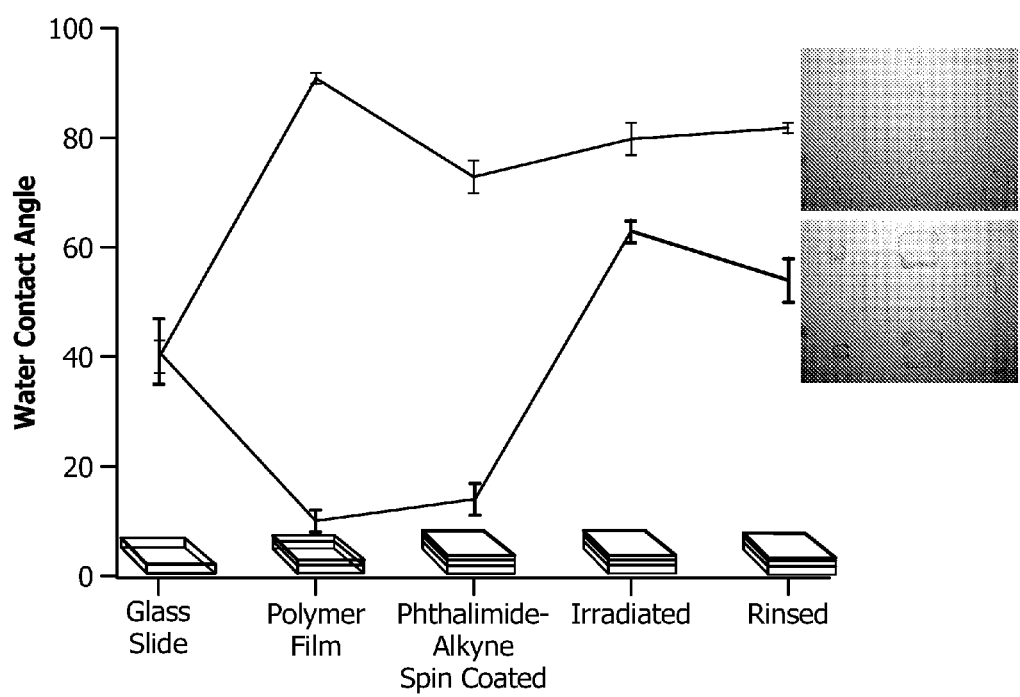
FIG. 11 shows the various contact angle measurements as the heterobifunctional molecules are applied and covalently bound to a polymer surface by irradiation for 30 minutes in accordance with certain embodiments.

FIG. 11 shows water contact angle measurements for glass, PS and PAA surface on glass, phthalimide-alkyne heterobifunctional molecule deposited on PS and PAA surfaces, followed by irradiation for 30 minutes, and subsequent rinsing. As shown, the contact angles further indicate successful attachment of the heterobifunctional molecules to the PAA and PS surfaces.

Discussion

The design of the phthalimide-alkyne small molecules incorporates a number of important characteristics that are helpful for the successful functionalization of polymer surfaces. Foremost, the photoactive anchor is a nearly universal anchoring moiety for polymer surfaces because of its well-known reaction with C—H bonds via the hydrogen abstraction mechanism. Excitation of the phthalimide carbonyl by ultraviolet light generates a biradical that abstracts a nearby hydrogen atom from the polymer to the carbonyl oxygen. The resultant radical on the polymer recombines with the remaining radical on the carbon of the phthalimide to generate a covalent bond between the phthalimide carbon and the polymer. Because the vast majority of polymers contain C—H bonds—which are not normally considered sites for reactive chemistry—such a photochemical method is ideally suited to the functionalization of numerous different types of polymers.

At the other end of the molecule, the alkyne and the TMS-protected alkyne offer a dual function for the appropriate functionalization of the surface. Most obviously they are both capable of reaction with azides via the Hüisgen 1,3-dipolar cycloaddition which is often catalyzed by a trace amount of copper(I). Though inert to the reaction in its protected form, the TMS-alkyne is facilely deprotected using a solution of potassium carbonate in $CH_2Cl_2$ and methanol. In addition to its orthogonal reactivity with azides, the alkyne group has a very low surface energy that aids in the orientation of the molecule in the preferred manor; the phthalimide end is oriented toward the polymer-film interface and the alkyne end is oriented to the air-film interface.

Previous research has most often functionalized a surface with an azide because its IR signature is more pronounced than that of the alkyne. For this application, however, the azide may be less desirable to functionalize on the surface because of its reactivity to irradiation. After excitation of the azide and loss of molecular nitrogen to generate a nitrene, ring insertion generally inactivates the nitrene forming an imine. Such reaction may lead to simultaneous inactivation of the click-functional end during attachment of the photoactive anchor to the polymer surface.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A heterobifunctional molecule comprising:
    a photoactive anchor that is capable of covalently binding to a surface by reacting with a C—H bond on the surface, wherein the photoactive anchor is selected from the group consisting of phthalimide, benzophenone, phenyl azide, xanthone, thioxanthone, sulfonyl azide, and phenyl diazirine;
    a terminal functional group having a click functionality, wherein the terminal functional group is selected from the group consisting of alkene, trimethylsilyl-protected alkyne, azide, nitrile, thiol, alkene, maleimide, streptavidin, biotin, antibody, antigen, integrin, fibronectin, epoxide, nucleophile, and thiiranium; and
    a spacer group that bridges the photoactive anchor and the terminal functional group, wherein the spacer is selected from the group consisting of oligomeric or polymeric forms of alkanes, alkane esters, alkane ethers, ethylene glycols, acetylenes, and phenylenes.

2. The heterobifunctional molecule of claim 1, wherein the photoactive anchor is on a first end of the heterobifunctional molecule, the terminal functional group is at a second end of the heterobifunctional molecule and the terminal functional group consists of the click functionality, and the spacer group bridges the photoactive anchor at the first end and the terminal functional group at the second end.

3. The heterobifunctional molecule of claim 1, wherein the photoactive anchor binds to the surface upon irradiation.

4. The heterobifunctional molecule of claim 1, wherein the photoactive anchor has a higher surface energy than the terminal functional group.

5. The heterobifunctional molecule of claim 1, wherein the photoactive anchor is a phthalimide and the terminal functional group is alkyne or a trimethylsilyl-protected alkyne.

6. The heterobifunctional molecule of claim 1, wherein the surface is the surface of a polymer.

7. A functionalized surface comprising:
a material that comprises one or more C—H bonds on a surface of the material;
the heterobifunctional molecule of claim 1 covalently bound to at least a portion of the surface of the material, wherein the heterobifunctional molecule has a click functionality; and
a functionalizing moiety bound to the heterobifunctional molecule using an orthogonal click functionality.

8. The functionalized surface of claim 7, wherein the functionalizing moiety is a biomolecule, analyte, fluorophore, polymer, nanoparticle, anti-microbial material, phospholipid, dye, or chelator.

9. The functionalized surface of claim 7, wherein the functionalizing moiety is selected from the group consisting of DNAs, peptides, antibodies, and receptors.

10. The functionalized surface of claim 7, wherein the photoactive anchor is a phthalimide and the terminal functional group is alkyne or a trimethylsilyl-protected alkyne.

11. A method for functionalizing a surface, the method comprising:
applying the heterobifunctional molecule of claim 1 to a surface of a material;
irradiating the heterobifunctional molecule; and
functionalizing the surface by reacting a functionalizing moiety with the heterobifunctional molecule using an orthogonal click functionality.

12. The method of claim 11, further comprising:
applying a mask having a desired pattern prior to said irradiating.

13. The method of claim 11, wherein the photoactive anchor is on a first end of the heterobifunctional molecule, the terminal functional group is at a second end of the heterobifunctional molecule and the terminal functional group consists of the click functionality, and the spacer group bridges the photoactive anchor at the first end and the terminal functional group at the second end.

14. The method of claim 11, wherein the photoactive anchor binds to the surface upon irradiation.

15. The method of claim 11, wherein the photoactive anchor has a higher surface tension than the terminal functional group.

16. The method of claim 11, wherein the photoactive anchor is a phthalimide and the terminal functional group is alkyne or a trimethylsilyl-protected alkyne.

17. The method of claim 11, wherein the material is a polymer.

18. The method of claim 11, wherein the functionalizing moiety is a biomolecule, analyte, fluorophore, polymer, nanoparticle, anti-microbial material, phospholipid, dye, or chelator.

* * * * *